(12) United States Patent
Blatt et al.

(10) Patent No.: US 7,097,868 B2
(45) Date of Patent: Aug. 29, 2006

(54) STABLE COATED MICROCAPSULES

(75) Inventors: Yoav Blatt, Rehovot (IL); Rika Pinto, Tel Aviv (IL); Oleg Safronchik, Ashdod (IL); Tanya Sedlov, Beer Sheva (IL); Morris Zelkha, Omer (IL)

(73) Assignee: Bio-Dar Ltd., Yavne (IL)

( * ) Notice: Subject to any disclaimer, the term of this patent is extended or adjusted under 35 U.S.C. 154(b) by 353 days.

(21) Appl. No.: 09/935,050

(22) Filed: Aug. 23, 2001

(65) Prior Publication Data
US 2003/0064133 A1 Apr. 3, 2003

(51) Int. Cl.
*A23L 1/302* (2006.01)
*A23L 1/303* (2006.01)
*A23L 1/0532* (2006.01)

(52) U.S. Cl. .............. 426/89; 426/72; 426/73; 426/98; 426/575; 426/601

(58) Field of Classification Search .............. 426/89, 426/98, 575, 518, 72, 73, 601
See application file for complete search history.

(56) References Cited

U.S. PATENT DOCUMENTS

| 3,565,559 | A |   | 2/1971  | Ryota et al. |              |
|-----------|---|---|---------|--------------|--------------|
| 4,389,419 | A | * | 6/1983  | Lim et al.   | ...... 426/72 |
| 4,710,384 | A |   | 12/1987 | Rotman       |              |
| 4,895,725 | A | * | 1/1990  | Kantor et al. | ...... 426/455 |
| 5,855,826 | A |   | 1/1999  | Lee et al.   |              |
| 6,146,671 | A |   | 11/2000 | Catron et al. |             |
| 6,555,544 | B1 | * | 4/2003 | Francois et al. | ...... 514/259.41 |
| 6,569,463 | B1 | * | 5/2003 | Patel        | ...... 424/497 |

FOREIGN PATENT DOCUMENTS

GB    2 192 171 A    1/1988

OTHER PUBLICATIONS

Goosen et al., "Injectable Microencapsulated Islet Cells as a Bioartificial Pancreas", *Applied Biochemistry and Biotechnology*, 1984, pp. 87–98, vol. 10.

* cited by examiner

*Primary Examiner*—Helen Pratt
(74) *Attorney, Agent, or Firm*—Browdy AndNeimark, PLLC

(57) ABSTRACT

A microencapsulated composition containing lipophilic compounds is prepared by reducing the particle size of the lipophilic compound in the presence of a surface active agent to form a first solution; preparing a solution of alkali metal alginate to form a second solution; combining the first and second solutions to form a third solution; adding the third solution dropwise to a fourth solution containing calcium ion, obtaining beadlets, and removing the formed beadlets from the fourth solution; rinsing the beadlets with an acidic solution and drying the beadlets; and coating the beadlets to obtain microcapsules.

25 Claims, No Drawings

STABLE COATED MICROCAPSULES

FIELD OF THE INVENTION

The present invention relates to microencapsulated compositions of lipophilic compounds, having improved stability and to a method or preparing said composition.

BACKGROUND OF THE INVENTION

Processes for encapsulating oils and oil soluble substances are well known in the art.

U.S. Pat. No. 4,389,419, for example, which is incorporated herein by reference, relates to a process for encapsulating oils and oil-soluble substances in multi-compartmentalized, mechanically stable microcapsules. The process comprises the steps of first forming an emulsion consisting of a continuous phase comprising an aqueous solution of an alkali metal alginate and optionally a water-soluble, alcohol-insoluble filler such as a polysaccharide, and a dispersed phase of an oleophilic substance such as one or more vitamins dissolved in an oil. The emulsion is then formed into droplets which are thereafter immersed in an alcoholic solution of multivalent cations, to produce a shape-retaining alginate matrix filled with precipitated polysaccharide and enclosing plural oil droplets. The vitamins are thereby protected from oxidative degradation and can be handled like conventional crystalline solids.

Algin is a polysaccharide found in brown algae. Alginates and their derivatives have become significantly important hydrocolloids and are applied in a wide variety of industrial fields.

Algin is a polysaccharide that contains $\beta$-(1→4)-D-mannuroic acid of structure I:

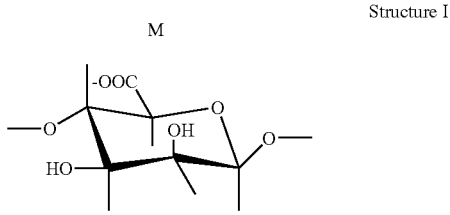

Structure I and $\alpha$-(1→4)-L-guluronic acid of the structure II:

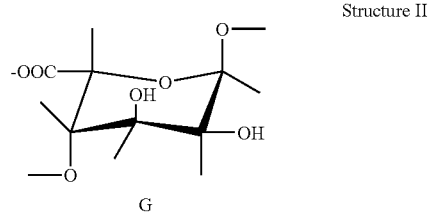

Structure II

Algin is a heterogeneous polymer consisting of the following three types of molecular blocks:

i) M-block, consisting of only M—M linking;
ii) G-block, consisting of only G—G linking; and
iii) Random block, M and G randomly linked.

Calcium alginate gel beads are used to entrap a wide variety of substances. The entrapment with calcium alginate is particularly favored because of the mild conditions employed add the nontoxicity of the reactants. Typically, the procedure simply involves dropping a 1–2% solution of sodium alginate into a 1–2% solution of calcium chloride. The alginate solution may be pumped through a small orifice, such as a needle, or rotating plate or vibrating droplets feeder and allowed to free-fall, producing a spherical bead, which gels upon contact with the calcium source. The beads then remain in the calcium bath until hardened.

Islets of Langerhans, the cells producing the insulin in the pancreas, may be entrapped in an alginate polycation microcapsule to allow small molecules such as glucose and other nutrients to diffuse freely, while preventing the passage of large molecules and cells. Physico-chemical properties of the microcapsules, such as shape, size and permeability, can be controlled (Goosen et al., *Applied Biotechnology and Bioengineering*, 10, 87–98, 1984).

According to U.S. Pat. No. 4,389,419, ". . . the amount of oil used may range broadly between 1% and close to 30%. However, at the higher end of the range, the stability of the oil-in-water emulsion is decreased, and the quality of the microcapsule is reduced." (column 3 lies 5–9).

BASF Health and Nutrition publication dated October 1997 reports a process for microencapsulation using gelatin. In this report, the mean particle size of the final product is approx. 250µ and the concentration of the active ingredient is up to 50%. However, the BASF process involves the use of gelatin, which is an undesirable limitation. Gelatin is purified mainly from pigs and cows which are susceptible to The Mad Cow disease and the Foot and Mouth disease.

U.S. Pat. No. 6,146,671 discloses a method for protecting a heat and/or oxygen-labile compound by encapsulation in a protective matrix of alginate and an additional polymeric material, which provides a single layer coating system. U.S. Pat. No. 6,146,671 further suggests the use of gelatin as a preferred protective polymer. Recently, the market is looking for materials which are not derived from animals which are susceptible to Mad Cow Disease.

In view of the above, the need for a stable, GMO-free, vegetable source alginate microcapsule having a high lipophilic compound content, small particle size with improved bioavailability, remains.

It is therefore the objective of the present invention to provide a microencapsulated formulation of lipophilic compounds which contains a relatively high lipophilic compound content with improved bioavailability and stability.

SUMMARY OF THE INVENTION

The present invention provides a process for the preparation of a microencapsulated composition containing lipophilic compounds comprising of the following steps:

(i) Particle size reduction of the lipophilic compound in the presence of a surface active agent;
(ii) Preparing a solution of alkali metal alginate.
(iii) Combining the solutions of step (i) and step (ii).
(iv) Adding dropwise the solution obtained from stage (iii) to a solution containing $Ca^{2+}$, obtaining beadlets, and removing the formed beadlets from said solution;
(v) Rinsing the beadlets with an acidic solution and drying;
(vi) Coating the beadlets obtained from step (v) to obtain the microcapsules, Optionally, a filler is added to the solution prepared in stage (i) and/or (ii).

The present invention, in one aspect, relates to a microencapsulated composition comprising of one or more lipophilic compound enveloped by a surfactant which is encapsulated in an alginate matrix and further coated with an outer coating, wherein the particle size of the lipophilic substance is not greater than 20 μm.

DETAILED DESCRIPTION OF THE INVENTION

The following description is illustrative of embodiments of the invention. The following description is not to be construed as limiting, it being understood that the skilled person may carry out many obvious variations to the invention.

Throughout the description, percentages of components are by weight, unless specifically noted differently. The term "particle size" also refers to the size drops of liquid substances.

It has surprisingly been found that lipophilic compounds treated with a surfactant and microencapsulated in an alginate matrix and then further coated by a protective layer, provides a stable microcapsule with a relatively large loading capacity of the lipophilic compound. Stability of the microcapsule in the present context refers to good containing properties, i.e. the encapsulation protects the lipophilic compound from exposure to oxidation and other conditions which may adversely effect the lipophilic compound. It would be expected that coating the lipophilic compound with three protective layers, as in the present invention would adversely effect the bioavailability of said compounds. However, it has further surprisingly been found that encapsulating the lipophilic compounds according to the present invention, wherein the particle size of said compounds is not greater than 20 μm, and rinsing the alginate beadlets with an aqueous acidic solution before the final drying of the beadlets, provides a microcapsule wherein the lipophilic compound displays improved bioavailability.

The lipophilic compounds suitable for the present invention are lipophilic compounds which are sensitive to heat or oxygenating conditions. Non-limiting examples of lipophilic compounds are carotenoids (e.g., lycopene, beta and alpha-carotene, lutein, astaxanthin, zeaxanthin), vitamin A, vitamin E, vitamin D, omega 3, omega 6 oils and mixtures thereof. Further lipophilic compounds suitable for the present invention are lipophilic compounds which have a taste or smell which is required to be masked, e.g., bitter tasting vitamins and fish oil. Throughout the description the term lipophilic compounds encompasses the foregoing definition and mixtures of said compounds.

According to a particular embodiment of the process of the present invention, a mixture containing 0.01% to 5% of a surfactant agent, 0.1% to 5% of a lipophilic compound, wherein said lipophilic compounds are selected from among a group comprising of lycopene, beta-carotene, lutein, alfacarotene, astaxanthin, zeaxanthin, vitamin A, vitamin E, vitamin D, omega 3 and omega 6 oils, or mixtures thereof, and 0% to 20%/of a filler is prepared. Said mixture is processed for size reduction of the particles of the lipophilic compounds. Wherein the lipophilic compound is in solid form said solid mixture is processed in a grinder and wherein the lipophilic compound is in liquid form said mixture is processed in a high shear mixer. The processing of the lipophlic compound with a surface active agent (surfactant) creates a coating of the surfactant around the particles of the lipophilic compound, i.e. a primary protective layer.

Following size reduction, a separate alkali metal alginate solution is prepared by dissolving an alkali metal alginate in water to provide a solution containing 0.5% to 10% of an alkali metal alginate, preferably 1.5% sodium alginate in water. The alkali metal alginate solution is mixed with the mixture containing the lipophilic compound. The resulting mixture is homogenized to provide a substantially homogenous emulsion or dispersion which is added drop-wise to a solution containing 0.2% to 5% of $Ca^{2+}$, preferably 1.5% calcium chloride.

The drop-wise addition is carried out such that the drops are not bigger than 1000 μm. Thus, upon contact of the drops with the $Ca^{2+}$ solution, beadlets of lipophilic-compound-containing alginate is formed. This creates a second protective layer for the lipophilic compound. The size of the beadlets can be controlled by controlling the size of the droplets. Preferably the size of the drops is adjusted so as to provide beadlets in the size range of about 100 μm to 450 μm.

The beadlets are then separated from the liquid by conventional separating means, e.g., screening, and rinsed with an aqueous acidic solution. The acidic solution is preferably a 0.1% to 10% solution of an acid selected from among a group comprising of citric, aspartic, acetic, ascorbic, lactic, phosphoric or hydrochloric acid. More preferably, said acidic solution is a 2.5% solution of citric acid or phosphoric acid in water. The rinsing with an acidic solution effects shrinkage of the beadlets and improves the bioavailability of the microencapsulated lipophilic compound.

The beadlets are then dried according to drying methods known in the art, preferably, by fluidized bed drying. "Drying" meaning lowering the water content below 10%. The dry beadlets are then coated with a coating material in a fluidized bed apparatus, according to the coating technique described in U.S. Pat. No. 4,710,384, incorporated herein by reference. Hence, a third coating layer is provided. Suitable coating materials for the final coating stage are cellulose derivatives, waxes, fats, proteins or polysaccharides. Non-limiting examples of cellulose derivatives suitable for coating material are: ethyl cellulose, hydroxy propyl cellulose, hydroxy propyl methyl cellulose and methyl cellulose. Waxes can be carnauba wax, candelila wax and beeswax. Fats can be hydrogenated vegetable oils, e.g. soybean and palm oil, mono and diglycedes, stearic, palmitic acids. Proteins can be albumins, zein, soy proteins or milk proteins. Polysaccharides can be starches, maltodextrins, pectins, xanthan gum, gum Arabic or carrageenan. According to a particular embodiment of the present invention, wherein there is no restriction regarding the use of products derived from animals, gelatin may be applied as a suitable protein for the third layer coating.

The operation of size reduction in stage (i) of the present invention may be effected in a liquid medium. The liquid medium may be water or other water miscible solvents wherein non-limitive examples of suitable liquids are alcohols e.g., methanol, ethanol, iso-propanol, acetone and ethyl acetate. Accordingly, the liquid is added to the solution of stage (i) which contains the lipophilic compound and surface active agent.

According to yet a further embodiment of the present invention, the drying and final coating are carried out in one step in a fluidized bed apparatus.

According to a particular embodiment of the present invention when the lipophilic compound is in liquid form, stage (i) of the process is carried out so that the drop size of the lipophilic compound is reduced to a size not greater than 20 μm, preferably in the range of 3 μm to 7 μm, and the mixture obtained from stage (i) is an emulsion or suspension.

In yet a further preferred embodiment of the present invention the lipophilic compound is selected from among a group consisting of beta-carotene, lycopene, alpha-carotene, lutein, astaxanthin, zeaxanthin, vitamin A, vitamin E, vitamin D, omega 3 and omega 6 oils, wherein the microcapsule contains 0.1% to 40% of said lipophilic compound or mixtures thereof.

Suitable fillers for use in stage (i) and/or (ii) of the process are selected from among a group comprising of polysaccharides e.g., pectin, starch, carageenan, gum Arabic, xanthan gum, carboxymetyl cellulose, methyl cellulose, hydroxypropyl cellulose, proteins from soybean, corn, milk or whey.

The term "surfactant agent" refers to any substance which has emulsifying, colloidal, stabilizing or dispersing qualities. Non-limiting examples of suitable surfactants can be non-ionic, anionic or cationic sufactants, e.g., alcohol alkoxylates; alcohol ethoxylates; alkylphenol alkoxylates; alkylphenol ethoxylates; alkyl polysaccharides,; block copolymers e.g., ethoxylated polypropylene oxides, alcoxylated ethylene diamine; esters e.g., glycerol mono and distearate, glycerol mono and dioleate; ethoxylated sorbitan esters and sorbitan esters, different proteins e.g. protein from soybean, corn or whey.

According to a particular embodiment of the present composition, the microencapsulated lipophilic-compound-containing composition contains 0.1% to 40% of a lipophilic compound selected from along beta-carotene, lycopene, alpha-carotene, lutein, astaxantin, zeaxanthin, vitamin A, vitamin E, vitamin D, omega 3 and omega 6 oils or mixtures thereof, wherein the particle size of the lipophilic compound is not greater than 10 μm, preferably between 2 μm and 5 μm. Said composition further comprises a surfactant, an alginate matrix which incorporates the surfactant-coated lipophilic compound and a coating which coats the lipophilic-compound-containing alginate matrix. The coating material is selected from among a group comprising of cellulose derivatives, waxes, fats, proteins and polysaccharides.

The microencapsulated compositions according to the present invention are suitable for tablet preparation, hard shell capsule filling and incorporating in different foods. According to a particular embodiment of the present invention, the lipophilic compounds or mixtures thereof employed herein may further comprise fillers, excipients or additives. Examples of suitable fillers are starch, pectins, carraginanes, xanthan gums, proteins, polyethylene glycols, cellulose derivatives (e.g., methyl cellulose, hydroxypropyl cellulose and ethyl cellulose) and other polysaccharides.

The microcapsule prepared according to the present invention comprises of three protective layers which protect the lipophilic compounds. The first protective layer is created by the surfactant; the second protective layer is created by the alginate matrix and the third layer is the final coating layer.

According to a farther aspect of the present invention. The present process is suitable for encapsulating lipophilic compounds which have a taste or smell which is required to be masked. This is particularly important for introducing lipophilic compounds into food stuff and beverages wherein said lipophilic compound has a taste or smell which is offensive to the consumer or does not correlate with the taste or smell of the food stuff and beverage. For example masking the taste of a bitter tasting lipophilic compound wherein said lipophilic is added to a sweet or salty food. This effect is achieved by the present process without inhibiting the bioavailability of the lipophilic compound.

The present invention is advantageous in that it provides microcapsules of lipophilic compounds with improved stability, relatively high content of the lipophilic compound and improved bioavailability of the lipophilic compound. These advantages are achieved by the process which provides a tee layer coating of lipophilic compound and by the small particle size of said compounds. The advantages of the present composition are also found in the improved mechanical properties of the microcapsules which are achieved by the third layer coating. Thus, the microcapsules of the present invention are also tablet grade, i.e. suitable for use in tableting. Furthermore the compositions of the present invention are gelatin free. Due to the fact that the common use of gelatin is obviated according to the present invention, the product of the present invention is from vegetable origin.

EXAMPLES

Example 1

Encapsulation of Beta-Carotene by the present invention was done as follows:

In the first step the following ingredients were taken:

| (a) | | |
|---|---|---|
| 1. | Natural beta-Carotene crystals (DSM) | 36.6 g. |
| 2. | Decaglyceryl monooleate | 17.4 g. |
| 3. | Sucrose palmitate | 17.4 g. |
| 4. | Water | 580.0 g. |

All ingredients were mixed and grinded together to form a homogenous suspension with particle size less than 5 microns.

In the second step the following ingredients were dissolved:

| (b) | | |
|---|---|---|
| 1. | Sodium Alginate | 180.0 gr. |
| 2. | Starch (from Peas) | 120.0 gr. |
| 3. | Water | 11420.0 gr. |

Suspension (a) and solution (b) were mixed together to form a homogenous suspension. The suspension was fed through a dispenser, installed above a 1.5% Calcium chloride solution in water. The spherical droplets, upon entering the solution, gel to form Beta-Carotene alginate matrix beads when retained in the solution for 5 to 30 minutes. The beadlets were collected by filtration and washed in 2.5% citric acid in water. The beadlets were dried and then coated in a fluidized bed dryer and coater. The coating material was made from the following ingredients:

| (c) | | |
|---|---|---|
| 1. | Hydroxypropylcellulose | 70.0 g. |
| 2. | Methanol | 177.0 g. |
| 3. | Acetone | 369.0 g. |

This process yielded coated dry spherical beads containing encapsulated β-Carotene. The particle size of 85% of the beads was between 150 microns and 425 microns.

Example 2

The process of Example 1 is repeated with a different composition of solution (b):

| | | |
|---|---|---|
| 1. | Sodium Alginate | 180.0 g. |
| 2. | Pectin (high ester) | 120.0 g. |
| 3. | Water | 11420.0 g. |

Example 3

Encapsulation of Lycopene was performed as follows:

The following material were ground and homogenized together at 40° C. until the particle size of the lycopene was in the range of 2–5 μm:

| | (a) | |
|---|---|---|
| 1. | Natural tomato oleoresin (20% Lycopene, Lycored)* | 139.0 g. |
| 2. | Ethanol | 150.0 g. |
| 3. | Decaglyceryl monooleate | 22.7 g. |

*Particle size of lycopene 50–110 μm

A second solution was made at 70° C.

| | (b) | |
|---|---|---|
| 1. | Sodium Alginate | 180.0 g |
| 2. | Sucrose palmitate | 22.7 g. |
| 3. | Starch (from Peas) | 120 g |
| 4. | Water | 12000.0 g |

Mixture (a) was added to solution (b) and mixed to form a homogenous suspension.

Example 5

Improved Bioavailability and Stability—Comparative Test

The microcapsules prepared by the present invention were tested for stability and bioavailability. Stability tests were done by incubating the microcapsules in pure oxygen atmosphere for 10 to 40 days at room temperature (25° C.) and then assay the microcapsules for their lipophilic compound content. Bioavailability was checked using a USP type 2 dissolution apparatus. The microcapsules were incubated in gastric fluid (0.1M HCl) for one hour at 37° C. with the paddles rotating at 75 RPM. Then the pH was raised to 7 with the addition of tri-sodium phosphate 0.2M solution. In addition, cholic acid 0.1% and SDS (sodium dodecyl sulfate) 0.1% were added to simulate an intestinal fluid. After another three hours the solution was sampled and filtered. The filtrate was assayed for the concentration of the lipophilic compound. The bioavailability was estimated by the percent of the lipophilic compound from the microcapsules that was dissolved in the simulated intestinal fluid.

Microcapsules prepared according to Example 1 were examined for bioavailability which was found to be 86%. A similar preparation in which the beta-carotene was not ground in the presence of the surfactant the bioavailability was 4%. This shows the importance of the first layer of coating and the particle size of the lipophilic compound in the bioavailability of the lipophilic compound.

When the microcapsules that were made as in Example 3 were tested for stability the lycopene content of the microcapsules was reduced in ten days in oxygen atmosphere by 7%. Similar microcapsules that were not washed in acidic solution but prepared similarly otherwise their lycopene content was lowered by 25% in ten days in oxygen atmosphere. This shows the importance of the acidic wash for the stability and bioavailability of the lipophilic compound.

Example 6

Tableting of the Microcapsules

The suitability of the beadlets for tableting, i.e. tablet grade was evaluated by tablet compression in a Korsch EKII single punch tablet press. The beadlets (30 g) were mixed with 190 g of microcrystalline cellulose, 2.25 g of magnesium stearate and 2.25 g of sodium starch glycolate. The mixture was compressed in the tablet press using a 12 mm die producing tablets of 680 mg in weight with strength of 12 kg. Using beadlets produced in Example 1 and 3 gave tablets spotted with dark red spots. When these tablets were put in oxygen atmosphere as mentioned above, no reduction in the concentration of beta-carotene (Example 1) or Lycopene (Example 3) was observed after 10 days. In comparison, beadlets that were not coated with hydroxypropyl cellulose were produced. These beadlets were identical to those made in Example 1 and 3 but were not coated with solutions (c) in each example. When these beadlets were compressed into tablets with the same composition, the tablets were stained orange indicating that the beta-carotene and the Lycopene were leaking out of the uncoated beadlets. In addition, these tablets show reduction in beta-carotene concentration (−30%) and in Lycopene concentration (−36%) in 10 days in oxygen atmosphere. This shows the importance of the third coating layer for the stability of the microencapsulated lipophilic compound and for its suitability to tablet compression.

While embodiments of the invention have been described by way of description, it will be apparent that the invention may be carried out with many modification, variations and adaptations, without departing from its spirit or exceeding the scope of the claims.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention

What is claimed is:

1. A process for the preparation of a composition containing at least one microencapsulated lipophilic compound comprising:

(i) particle size reduction of the lipophilic, compound in the presence of (1) a surface active agent and (2) water or a water miscible solvent or a mixture thereof, to provide a first composition comprising an emulsion or suspension of surface active coated lipophilic particle in said water or water miscible solvent or mixture thereof;

(ii) providing a solution of alkali metal alginate;

(iii) combining said first composition and the alkali metal alginate solution to provide a second composition;

(iv) adding dropwise the second composition to a solution containing $Ca^{2+}$, thereby obtaining beadlets having a second coating of Calcium alginate, and removing the formed beadlets from said solution;

(v) rinsing the beadlets with an 0.1% to 10% acidic solution and dying said beadlets to obtain dried beadlets; and (vi) coating the dried beadlets with a third coating material to obtain microcapsules containing said lipophilic compound, said coating material being of vegetable origin and being selected from the group consisting of cellurose derivatives, waxes, fats, proteins and polysaccharides.

2. A process according to claim 1, wherein the particle size of the lipophilic compound is reduced to a particle size not greater than 20 μm.

3. A process according to claim 2 wherein the particle size of the lipophilic compound is reduced to a particle size not greater than 10 μm.

4. A process according to claim 1, wherein the alkali metal alginate is sodium or potassium alginate.

5. A process according to claim 1 wherein a filler is added to stage (i).

6. A process according to claim 1, wherein the lipophilic compound is selected from the group consisting of lycopene, beta and alpha-carotene, lutein, astaxanthin, zeaxanthin, vitamin A, vitamin E, vitamin D, omega 3 oils, omega 6 oils and mixtures thereof.

7. A process according to claim 1 wherein a filler is added to stage (ii).

8. A process according to claim 1, wherein the lipophilic compound containing alginate beadlets are in the size range of 100 to 425 μm.

9. A process according to claim 1 wherein the acidic solution is an acidic aqueous solution of an acid selected from the group consisting of citric, aspartic, acetic, ascorbic, lactic, phosphoric and hydrochloric acids.

10. A process according to claim 1, wherein the third coating is said cellulose derivative comprising hydroxypropylcellulose.

11. A method for incorporating lipophilic compounds in food stuff comprising of encapsulating the lipophilic compound according to the process of claim 1 and adding the encapsulated composition to food stuff.

12. A method for masking the flavor and/or smell of lipophilic compounds comprising encapsulating the lipophilic compound according to the process of claim 1.

13. The method of claim 1, wherein said rinsing of said beadlets with an acidic solution is sufficient to effect shrinkage of said beadlets.

14. The process of claim 1, wherein said solution of alkali metal alginate comprises 0.5% to 10% of an alkali metal alginate in water and
said solution containing $Ca^{2+}$ contains 0.2% to 5% of $Ca^{2+}$.

15. A microencapsulated composition comprising of one or more lipophilic compounds enveloped by a surfactant agent, encapsulated in an alginate matrix providing beadlets of size about 100 μm to 450 μm, and further coated with an outer coating of vegetable origin, wherein the particle size of the lipophilic substance is not greater than 20 μm, said composition being made by the process of claim 1.

16. A composition according to claim 15 wherein the lipophilic compound is selected from the group consisting of lycopene, beta and alpha-carotene, lutein, astaxanthin, zeaxanthin, vitamin A, vitamin E, vitamin D, omega 3 oils, omega 6 oils and mixtures thereof.

17. A composition according to claim 15 wherein the particle size of the lipophilic compound is not greater than 10 μm.

18. A composition according to claim 17 wherein the particle size not greater than 5 μm.

19. A composition according to claim 15 wherein the size of the microcapsules is in the range of 50 μm to 950 μm.

20. A composition according to claim 19 wherein the size of the microcapsules is in the range of 100 μm to 450 μm.

21. A composition according to claim 15 comprising 0.1% to 40% of a lipophilic compound or mixtures thereof.

22. A composition according to claim 15 wherein the outer coating is a material selected from the group consisting of cellulose derivatives, waxes, fats, proteins and polysaccharides.

23. A composition according to claim 21 wherein the outer coating is hydroxypropylcellulose.

24. A composition according to claim 15 wherein said composition is tablet grade.

25. A process for preparing a composition containing at least one microencapsulated liquid lipophilic compound, comprising:

(i) particle size reduction of the liquid lipopihlic compound, in the presence of a surface active agent, and optimally a filler in a liquid medium of (1) water, (2) a water-miscible liquid, or (3) a mixture of water and water-miscible liquid, thereby providing a suspension or emulsion wherein particles of the lipophilic compound have a particle size not greater than 10 μm and the particles are coated with a first coating of said surface active agent;

(ii) providing a solution of an alkali metal alginate optionally containing a filler;

(iii) combining said suspension or emulsion and the solution of alkali metal alginate to provide a second suspension or emulsion;

(iv) adding dropwise the second suspension or emulsion to a solution containing $Ca^{2+}$ thereby obtaining beadlets in liquid, said beadlets having a second coating of calcium alginate thereon and having a size of about 100 μm to 450 μm, and removing said beadlets from said liquid;

(v) rinsing said beadlets with an 0.1% to 10% acidic solution and drying said beadlets to obtain dried beadlets;

(vi) coating the dried beadlets with a coating material to provide a third coating, thereby obtaining microcapsules of 50–950 μm in particle size containing said lipophilic compound, wherein said microcapsules comprise said second and third coatings, wherein said coating material is of vegetable origin.

* * * * *